United States Patent [19]

Narayanan et al.

[11] Patent Number: 5,928,992
[45] Date of Patent: Jul. 27, 1999

[54] SOLID DELIVERY SYSTEM (SDS) FOR ACTIVE AGRICULTURAL CHEMICALS

[75] Inventors: Kolazi S. Narayanan, Wayne, N.J.; Domingo Jon, New York, N.Y.; Robert M. Ianniello, Oak Ridge, N.J.

[73] Assignee: ISP Investments Inc., Wilmington, Del.

[21] Appl. No.: 08/850,792

[22] Filed: May 2, 1997

[51] Int. Cl.$^6$ ........................................ A01N 25/02
[52] U.S. Cl. .................................. 504/116; 504/118
[58] Field of Search ............................ 504/116, 118

[56] References Cited

U.S. PATENT DOCUMENTS

| | | | |
|---|---|---|---|
| 5,230,892 | 7/1993 | Feyen et al. | 424/409 |
| 5,300,529 | 4/1994 | Narayanan | 514/788 |
| 5,338,762 | 8/1994 | Narayanan | 514/788 |
| 5,389,297 | 2/1995 | Narayanan | 252/312 |
| 5,427,795 | 6/1995 | Feyen et al. | 424/409 |
| 5,698,211 | 12/1997 | Narayanan | 424/409 |
| 5,731,264 | 3/1998 | Narayanan et al. | 504/116 |

*Primary Examiner*—Jose' G. Dees
*Assistant Examiner*—Sabiha N. Qazi
*Attorney, Agent, or Firm*—William J. Davis; Walter Katz; Marilyn J. Maue

[57] ABSTRACT

This invention relates to a solid delivery system (SDS) for active agricultural chemicals, and, more particularly, to a bioenhanced, stable SDS for sulfonyl and sulfamoylurea agricultural chemicals capable of forming aqueous microdispersions or tank mixes thereof suitable for application to a plant site.

2 Claims, No Drawings

SOLID DELIVERY SYSTEM (SDS) FOR ACTIVE AGRICULTURAL CHEMICALS

BACKGROUND OF THE INVENTION

1. Field of the Invention

This invention relates to a solid delivery system (SDS) for active agricultural chemicals, and, more particularly, to a bioenhanced, stable SDS for sulfonyl and sulfamoylurea agricultural chemicals capable of forming aqueous microdispersions or tank mixes thereof suitable for application to a plant site.

2. Description of the Prior Art

Sulfonyl and sulfamoylurea (SU) herbicides are very susceptible to hydrolysis in water or in admixture with other polar organic solvents which promote proton exchange between such chemicals and the solvent. Particularly, both the sulfonyl and sulfamoylurea compounds have a labile sulfonamide bridge which decomposes readily in water. Accordingly, stabilized liquid emulsifiable concentrates of such herbicides have been developed which when added to water to form a tank mix are suitable for application to a plant site. Such liquid emulsifiable concentrates are described by Narayanan et al. in copending U.S. patent application Ser. No. 08/733,285, filed Oct. 17, 1996.

Narayanan, in U.S. Pat. No. 5,389,297, also has described an inert matrix composition in the form of a free-flowing, high melting solid suitable for making a microemulsifiable concentrate by slurrying the active with a small amount of water, and freeze-drying. This concentrate will provide an aqueous microemulsion upon dilution with tank mix water. However, for sulfonyl and sulfamoyl ureas, as described in this invention, it is more advantageous to keep these actives and water apart until the final application step, so as to minimize the hydrolysis effect on such actives, while maximizing the bioenhancing capability of the N-octyl pyrrolidone component of the inert matrix composition on these actives.

SUMMARY OF THE INVENTION

What is described herein is a bioenhanced, stable solid carrier system for one or more sulfonyl or sulfamoyl urea agricultural chemicals suitable for forming an aqueous microdispersed tank mix upon dilution with water, which comprises, by weight, (a) 80–99.5% of an inert matrix composition comprising 10–50% of a $C_6$–$C_{18}$ alkyl pyrrolidone, about 5–50% of an anionic surfactant and about 10–70% of a water-soluble, high melting organic compound containing a dissociable proton which can complex with said pyrrolidone, a melting point of >100° C. a molecular weight of $\leq 500$, and a water solubility of at least 10%, which is selected from the group consisting of hydroxy acids, amino acids, sugars and amides, and (b) 1–20% of said agricultural chemical, optionally with a diluent agricultural chemical.

A further feature of the invention is an aqueous dispersion tank mix comprising dilution water in an amount sufficient to reduce the concentration of the agriculturally active ingredient to between a few ppm and 1% by weight.

Still another aspect of the invention is a method of making such systems which comprises admixture (a) and (b) as separate components.

DETAILED DESCRIPTION OF THE INVENTION

In accordance with the invention, the SDS includes (a) an inert matrix composition which comprises a higher lactam, i.e. a $C_6$–$C_{18}$ alkylpyrrolidone, e.g. N-octylpyrrolidone, N-isooctylpyrrolidone or N-dodecylpyrrolidone, or mixtures thereof. N-octylpyrrolidone is preferred. The lactam is present in an amount of about 10–50%, preferably 15–40%, and most preferably, 20–30%, by weight.

The second component is an anionic surfactant which is typified by an alkali metal salt of a $C_8$–$C_{22}$ aliphatic surfactant such as sodium dodecyl sulfate, or an alkyl aromatic sulfate, or sulfonates, ethoxylated derivatives of the above, alkylphenyl ethoxylated phosphate esters, tristyryl phenyl ethoxylated phosphate esters and the like. Sodium dodecyl sulfate is preferred. The anionic surfactant is present in the amount of about 10–50%, preferably 20–45%, and most preferably, 25–35%, by weight.

The third component is a complexing agent which is characterized by being an organic compound having a melting point of >100° C., a molecular weight of $\leq 500$, a water solubility of at least 10%, and being capable of hydrogen-bonding with the higher alkyl pyrrolidone. Suitable complexing agents for use herein have a dissociable proton which are present in hydroxy acids, such as lactic or citric acid; amino acids, such as glycine; sugars, such as lactose, sucrose, glucose or fructose; or amides, such as urea. The complexing agent is present in an amount of about 10–70%, preferably 30–60%, and most preferably, 25–50%, by weight.

Suitably a small amount of water is added to the mixture of components of (a), and the mixture is sprayed, freeze-dried or fluidized to form a solid.

Component (a) then is provided in the form of a free-flowing, high-melting solid, which is usually a granular, hydroscopic, or crystalline solid having a melting point of >100° C.

The (a) component then is admixed separately with (b), the SU, to form the desired SDS. Generally the SDS comprises about 80–99.5%, by weight, of (a) and 0.5–20% of (b), preferably 2–15%, and most preferably 3–10% of the SU. Optionally dispersant and/or wetting agents may be included in the SDS to assist in the formation of aqueous dispersions thereof upon dilution thereof with tank mix water. Optionally a hydrophobic polymer, or an inorganic mineral can be added to make the SDS less hydroscopic.

Typical active agricultural chemicals for use herein are shown below.

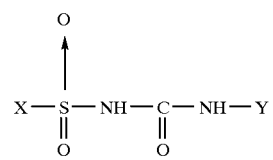

where X and Y are selected from the following:

| X | Y | NAME | |
|---|---|---|---|
| 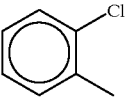 | 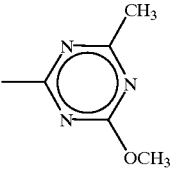 | Chlorsulfuron | Du Pont |
| 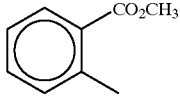 | 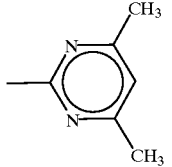 | Sulfometuron methyl | Du Pont |
| 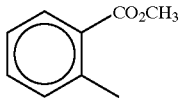 | 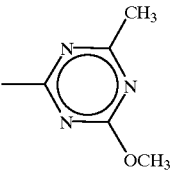 | Metsulfuron methyl | Du Pont |
| 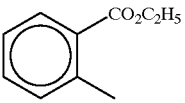 | 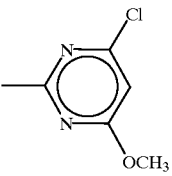 | Chlorimuron ethyl | Du Pont |
| 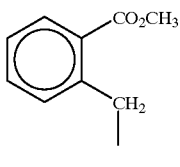 | 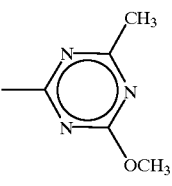 | Bensulfuron methyl | Du Pont |
| 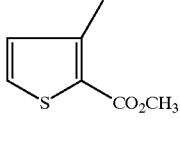 | 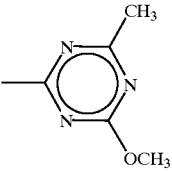 | Thifensulfuron methyl | Du Pont |
| 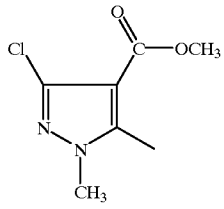 | 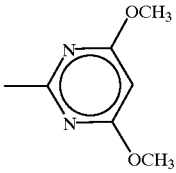 | Halosulfuron methyl | Nissan/Monsanto |
| 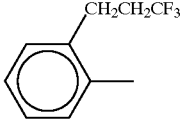 | 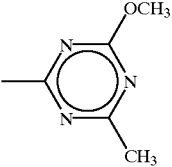 | Prosulfuron | Ciba Geigy |

-continued

| X | Y | NAME | |
|---|---|---|---|
| (2-methylphenyl with -C(=O)-OCH₃) | pyrimidine with OCHF₂, OCHF₂ | Primisulfuron methyl | Ciba Geigy |
| (2-methylphenyl with -OCH₂CH₂Cl) | triazine with OCH₃, CH₃ | Triasulfuron | Ciba Geigy |
| (phenyl with OCH₂CH₃ and -O-) | pyrimidine with OCH₃, OCH₃ | Ethoxysulfuron | Agrevo |
| (phenyl with cyclopropyl-C(=O)- and -NH-) | pyrimidine with OCH₃, OCH₃ | Cyclosulfamuron | Am Cy |
| (CH₃-S(=O)₂-N(CH₃)-) | pyrimidine with OCH₃, OCH₃ | Amidosulfuron | Agrevo |
| (2-methylphenyl with -C(=O)-OCH₃) | triazine with CH₃, CH₃ | DPXL₅₃₀₀ | Du Pont |
| (2-methylpyridine with -C(=O)N(CH₃)₂) | triazine with OCH₃, OCH₃ | Nicosulfuron | Du Pont |
| (2-methylpyridine with -SO₂CH₂CH₃) | pyrimidine with OCH₃, OCH₃ | Rimsulfuron | Du Pont |

-continued

| X | Y | NAME | |
|---|---|---|---|
| 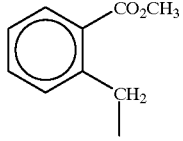 | 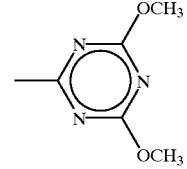 | Londax | Du Pont |
| 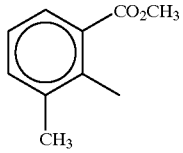 | 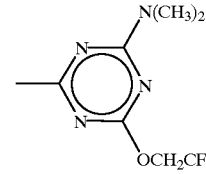 | Triflusulfuron methyl | Du Pont |
| 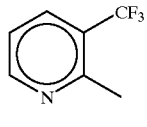 | 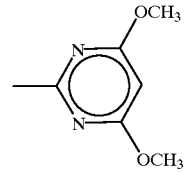 | Flazasulfuron | Ishihara |
| 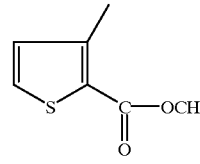 | 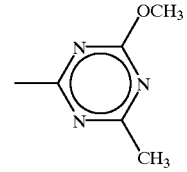 | Trifensulfuron methyl | Du Pont |

Sulfonylurea herbicides are effective at very low doses, i.e. at a rate of application of only grams per acre. However, it is important to avoid an overdose during use. For this reason, sulfonylureas generally are used in combination with a diluent agchemical in an amount of about 20–50% by weight of the concentrate. Such diluent agchemicals usually have broad spectrum activity at a dosage rate of lbs per acre. Another advantage of using diluent agchemicals in the concentrate is that while sulfonylureas are available commercially only as solids, the diluent agchemical can be obtained in liquid form, e.g. as an emulsifiable concentrate. Accordingly, their admixture will provide a diluted liquid premix of the active for transport and use in preparing the dispersion tank mix of the invention.

Some examples of diluent agchemicals for use herein include:

(1) Phenoxy compounds:
  e.g. phenoxy acetates (MCPA esters), phenoxy propionates, and phenoxy butyrates (MCPB esters);
(2) Benzoates (e.g. Dicamba);
(3) Chloroacetamide/chloroacetanilides (e.g. Alachlor, Acetachlor, and Metolachlor);
(4) Triazine derivatives (e.g. Metrubuzin), Triazinone (e.g. Metamitron);
(5) Carbanilates (e.g. Phenmedipharm);
(6) Thiocarbamates (e.g. Thibencarb); and
(7) Phenylurea (e.g. Linuron and Diuron).

What is claimed is:

1. An aqueous dispersion tank mix which comprises, by weight, (a) 80–99.5% of an inert matrix composition in the form of a free-flowing, high melting solid comprising 10–50% of a $C_6$–$C_{18}$ alkyl pyrrolidone, about 5–50% of an anionic surfactant and about 10–85% of a water-soluble, high melting organic compound containing a dissociable proton which can complex with said pyrrolidone, a melting point of >100° C. a molecular weight of ≦500, and a water solubility of at least 10%, which is selected from the group consisting of hydroxy acids, amino acids, sugars and amides, (b) 1–20% of one or more sulfonyl or sulfamoylurea active agricultural chemicals, with a diluent agricultural chemical, and (c) dilution water in an amount sufficient to reduce the concentration of said sulfonyl or sulfamoylurea to between a few ppm and 1% by weight.

2. A system according to claim 1 wherein said high melting organic compound is urea.

* * * * *